(12) United States Patent
Vatner et al.

(10) Patent No.: US 7,846,683 B2
(45) Date of Patent: Dec. 7, 2010

(54) METHOD FOR IDENTIFYING AGENTS WHICH MODULATE CELL GROWTH OR SURVIVAL

(75) Inventors: Stephen F. Vatner, New York, NY (US); Christopher Depre, New York, NY (US)

(73) Assignee: University of Medicine and Dentistry of New Jersey, New Brunswick, NJ (US)

( * ) Notice: Subject to any disclaimer, the term of this patent is extended or adjusted under 35 U.S.C. 154(b) by 0 days.

(21) Appl. No.: 11/575,887

(22) PCT Filed: Sep. 23, 2005

(86) PCT No.: PCT/US2005/034228

§ 371 (c)(1),
(2), (4) Date: Oct. 5, 2007

(87) PCT Pub. No.: WO2006/036822

PCT Pub. Date: Apr. 6, 2006

(65) Prior Publication Data

US 2008/0096237 A1 Apr. 24, 2008

Related U.S. Application Data

(60) Provisional application No. 60/612,837, filed on Sep. 24, 2004.

(51) Int. Cl.
*C12Q 1/48* (2006.01)
(52) U.S. Cl. ........................................................ 435/15
(58) Field of Classification Search ........................ None
See application file for complete search history.

(56) References Cited

U.S. PATENT DOCUMENTS 5,962,262 A * 10/1999 Hillman et al. ............ 435/69.1

FOREIGN PATENT DOCUMENTS

WO WO0111012 A2 * 2/2001

OTHER PUBLICATIONS

Gober et al (J Biological Chemistry, Epub Jun. 26, 2003, vol. 278, p. 37600-37609).*
Gober et al, Journal of Biological Chemistry, 2003, 278:37600-37609, IDS.*
Li et al, Oncogene, 2007, 26:3521-3531.*
Tockman et al (Cancer Res., 1992, 52:2711s-2718s).*
Bowie et al (Science, 1990, 247:1306-1310).*
Gober et al (Journal of Biochemistry, 2003, 278:37600-37609).*
Li et al (Oncogene, 2007, 26:3521-3531).*
Cantley, Lewis C., "The Phosphoinositide 3-Kinase Pathway", Science 2002 296:1655-1657.
Depre et al., "Gene program for cardiac cell survival induced by transient ischemia in conscious pigs", Proc. Natl. Acad. Sci. USA 2001 98(16):9336-9341.
Depre et al., "Program of Cell Survival Underlying Human and Experimental Hibernating Myocardium", Circ Res 2004 95:433-440.
Depre et al., "Glucose for the Heart", Circulation 1999 99:578-588.
Depre et al., "H11 Kinase Is a Novel Mediator of Myocardial Hypertrophy In Vivo", Circ Res. 2002 91:1007-1014.
Gober et al., "Forced Expression of the H11 Heat Shock Protein Can Be Regulated by DNA Methylation and Trigger Apoptosis in Human Cells", J. Biol. Chem. 2003 278(39):37600-37609.
Hase et al., "H11 has dose-dependent and dual hypertrophic and proapoptotic functions in cardiac myocytes", Biochem. J. 2005 388:475-483.
Hay and Sonenberg 2004 Genes Dev. 18:1926-1945.
Kappe et al., "Characterization of two novel human small heat shock proteins:protein kinase-related HspB8 and testis-specific HspB9", Biochimica et Biophysica Acta 1520 2001 1-6.
Knowlton, A.A., "Mutation of Amino Acids 246-251 Alters Nuclear Accumulation of Human Heat Shock Protein (HSP) 72 with Stress, But Does Not Reduce Viability", J Mel Cell Cardiol 1999 31:523-532.
Russell III et al., "AMP-activated protein kinase mediates ischemic glucose uptake and prevents postischemic cardiac dysfunction, apoptosis, and injury", The Journal of Clinical Investigation 2004 114(4):495-503.
Smith et al., "A Novel Human Gene Similar to the Protein Kinase (PK) Coding Domain of the Large Subunit of Herpes Simplex Virus Type 2 Ribonucleotide (ICP10) Codes for a Serine-Threonine PK and Is Expressed in Melanoma Cells", J. Biol. Chem. 2000 275(33):25690-25699.
Wange et al., "Increased expression of H11 kinase stimulates glycogen synthesis in the heart", Mol Cell Biochem 2004 265:71-78.
Yu et al., Expression analysis and chromosomes location of a novel gene (H11) associated with the growth of human melanoma cells, International Journal of Oncology 2001 18:905-911.

* cited by examiner

*Primary Examiner* — Laura B Goddard

(57) ABSTRACT

The present invention relates to a method for identifying an agent. for modulating cell growth or survival. The method involves the identification of an agent which modulates the net ratio of nuclear-localized versus cytosolic-localized H11 kinase or mutant H11 kinase in a cell. A method for diagnosing a cancer associated with H11 kinase or Akt activation in a subject is also provided.

2 Claims, 2 Drawing Sheets

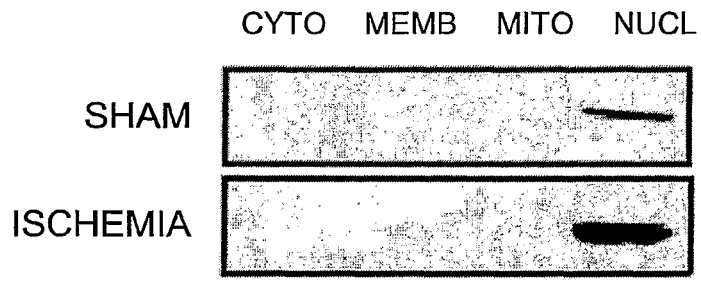
FIG. 2B
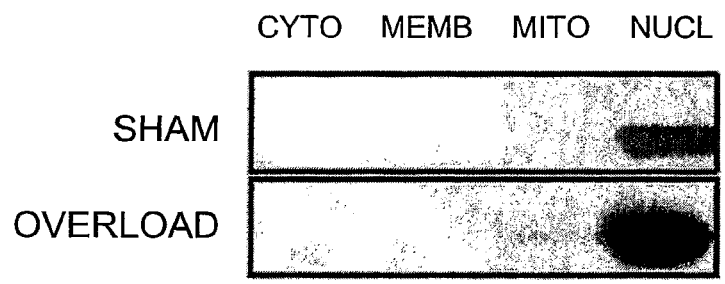
FIG. 2C
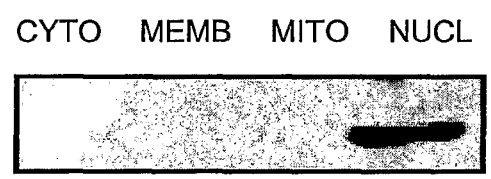
FIG. 2D
Melanoma
```
GAC TTG ACA GCC TCT TGG CCC GAC TGC GCT CTG CCT CGT CTC TCC TCC GCC
 D   L   T   A   S   W   P   D   C   A   L   P   R   L   S   S   A
```
Heart
```
GAC TTG ACA GCC TCT TGG CCC GAC TGG GCT CTG CCT CGT CTC TCC TCC GCC
 D   L   T   A   S   W   P   D   W   A   L   P   R   L   S   S   A
43                                                                59
```
FIG. 3

METHOD FOR IDENTIFYING AGENTS WHICH MODULATE CELL GROWTH OR SURVIVAL

INTRODUCTION

This application claims the benefit of priority from U.S. provisional patent application Ser. No. 60/612,837, filed Sep. 24, 2004, the contents of which is incorporated herein by reference in their entirety.

This invention was made in the course of research sponsored by the National Institutes of Health (Grant Nos. HL33065, AG 14121, HL 33107, PO1 HL 69020, and HL 072863). The U.S. government may have certain rights in this invention.

BACKGROUND OF THE INVENTION

H11 kinase is the eukaryotic homologue of the viral protein ICP10, an activator of the Ras pathway, which is responsible for the growth and neoplastic transformation of immortalized eukaryotic cells infected by Herpes Simplex Virus Type 2 (HSV2) (Smith et al. (2000) *J. Biol. Chem.* 275:25690-25699). Similarly, H11 kinase overexpression has been linked to different forms of neoplasia, including melanoma (Smith et al. (2000) supra) and breast cancer (Charpentier et al. (2000) *Cancer Res.* 60:5977-5893). However, in normal tissues, H11 kinase is predominantly expressed in heart and skeletal muscle (Kappe et al. (2001) *Biochim. Biophys. Acta.* 1520:1-6; Depre et al. (2002) *Circ. Res.* 91:1007-1014), where its precise function remains unknown.

The upregulation of H11 kinase gene and protein expression in a model of prolonged and stable left ventricular hypertrophy in the dog heart (Depre et al. (2002) supra) suggests that H11 kinase may participate in mechanisms of cell growth. Accordingly, a cardiac-specific transgenic mouse overexpressing H11 kinase was generated, which developed myocardial hypertrophy (Depre et al. (2002) supra). In addition, it has been shown that H11 kinase expression increases in a swine model of reversible ischemia (stunning) together with a cluster of genes promoting cell survival (Depre et al. (2001) *Proc. Natl. Acad. Sci. USA.* 98:9336-9341). H11 kinase expression has also been shown to increase in the heart as well under conditions of long-term ischemia, referred to as myocardial hibernation (Depre, et al. (2004) *Circ. Res.* 95:433-44). Further, H11K activates the serine/threonine kinase Akt/PKB, which can prevent cell death through an inhibition by phosphorylation of pro-apoptotic effectors, including glycogen synthase kinase-3β (GSK-3β), caspase-9, Bad and the transcription factor forkhead (Cantley (2002) *Science* 296:1655-1657). H11K has also been found to promote glucose metabolism in the heart in vivo (Wang, et al. (2004) *Mol Cell Biochem.* 265:71-78). Increased reliance upon glucose represents a metabolic survival response to ischemia (Depre, et al. (1999) *Circulation* 99:578-588), which is complementary to the anti-apoptotic mechanisms of Akt. The major activator of glucose utilization in the ischemic heart is the 5'AMP-activated protein kinase (AMPK), which promotes cell survival by a switching to anaerobic glucose utilization (Russell, et al. (2004) *J. Clin. Invest.* 114:495-503). Although Akt and AMPK appear complementary in promoting cell survival, they have an opposite effect on cardiac cell growth through a reciprocal regulation of the mammalian target of rapamycin (Hay and Sonenberg (2004) *Genes Dev.* 18:1926-1945). Thus, based on these observations, H11 kinase may have cytoprotective effects, which could promote cell survival and prevent irreversible ischemic damage in stunned myocardium. In contrast, overexpression of H11 kinase in vitro in different cell types has been shown to promote apoptosis (Gober et al. (2003) *J. Biol. Chem.* M303834200). Therefore, the mechanism by which H11 kinase controls cardiac cell survival and death remains to be elucidated.

SUMMARY OF THE INVENTION

The present invention provides a method for identifying an agent useful in modulating cell growth or survival, particularly cardiac cells. The method involves contacting a host cell containing H11 kinase or a mutant H11 kinase with a test agent and determining the net ratio of nuclear-localized versus cytosolic-localized H11 kinase or mutant H11 kinase in said cell as compared to a cell not contacted with the test agent. An increase in the nuclear to cytosolic ratio in the cell contacted with the agent as compared to the cell not contacted with the agent indicates that said agent increases cell growth or survival. Conversely, a decrease in the nuclear to cytosolic ratio in the cell contacted with the agent as compared to the cell not contacted with the agent indicates that said agent decreases cell growth or survival or increases cell death. Agents identified by the method of the invention and the use thereof in modulating cell growth or survival are also provided.

The present invention further provides a method for diagnosing a cancer associated with H11 kinase or Akt activation in a subject. The method involves detecting the presence of a $Trp^{51} \rightarrow Cys$ mutant of H11 kinase in a sample of a subject thereby diagnosing a cancer associated with H11 kinase or Akt activation in the subject. In particular embodiments, the method is carried out via detecting nucleic acid sequences encoding the $Trp^{51} \rightarrow Cys$ mutation or using an antibody which specifically recognizes a $Trp^{51} \rightarrow Cys$ mutant of H11 kinase.

BRIEF DESCRIPTION OF THE DRAWINGS

FIG. 2 shows the subcellular distribution of H11 kinase in heart from mouse, large mammals and human. FIG. 2B, increased expression of H11 kinase protein in swine heart after 90 minutes ischemia and 1 hour reperfusion compared to control (sham) animals (n=5 per group). FIG. 2C, increased expression of H11 kinase protein in chronic pressure overload canine heart specifically in the nuclear fraction. FIG. 2D, distribution of H11 kinase expression in a sample of human heart taken at the time of cardiac transplantation.

FIG. 3 shows a mutation in the nucleotide sequence and amino acid sequence of H11 kinase found in melanoma cells (SEQ ID NO:4 and SEQ ID NO:5, respectively) and wild-type heart cells (SEQ ID NO:6 and SEQ ID NO:7, respectively).

DETAILED DESCRIPTION OF THE INVENTION

Figure 1:
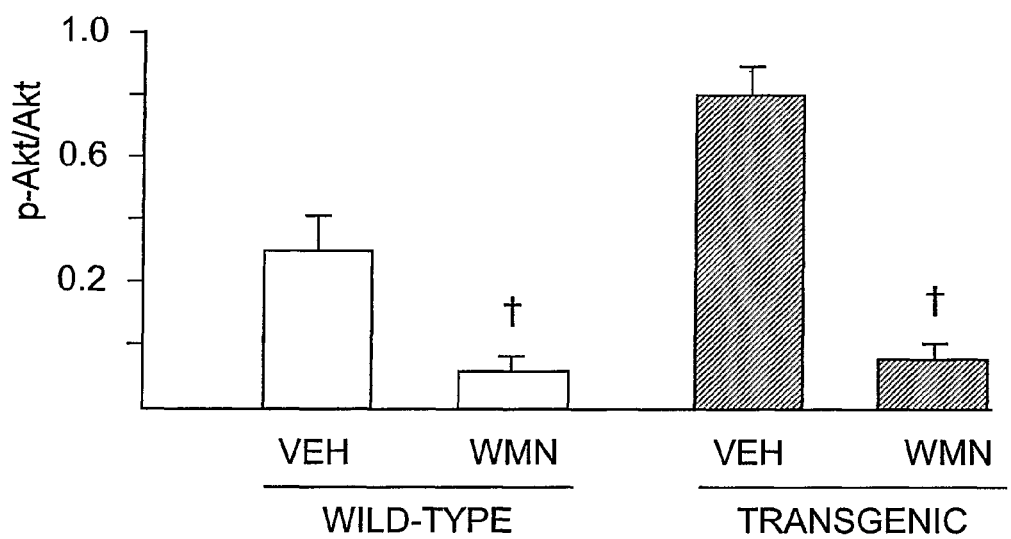
FIG. 1 shows Akt expression and phoshorylation measured in wortmannin (Wmn)-treated versus vehicle (Veh)-treated wild-type and transgenic mice. n=4 per group; **, P<0.01; †, P<0.01 vs corresponding Veh.

The role of H11 kinase in cell survival and death was investigated using a transgenic mouse model and cardiac myocytes in culture. Cardiac overexpression of H11 kinase in a transgenic mouse markedly protected the heart against irreversible damage to the same extent as ischemic preconditioning, the most powerful cardioprotective mechanism described to date. Cardioprotection by H11 kinase was associated with the coordinated activation of complementary growth and survival mechanisms as determined by heat-shock protein expression and Akt/mTOR signaling. H11 kinase expression was found in both the cytosol and the nucleus of heart from wild-type mice, but in the transgenic mouse, the cytoprotective effect correlated with a nuclear accumulation of the protein. Reciprocally, a cytosolic overexpression of H11 kinase in isolated cardiac myocytes inhibited Akt and $p70^{S6K}$, and promoted cell death. In larger mammals, H11 kinase largely predominated in the nucleus of the cardiac myocytes, where its expression increased during ischemia. Therefore, H11 kinase, and proteins which interact with H11 kinase, represent a novel mechanism of cell survival by the activation of complementary pathways of cytoprotection. Depending on subcellular localization, H11 kinase and Akt act to promote survival when located in the nucleus and as tumor suppressors when located in the cytosol.

Cardiac cell growth and survival was analyzed using a mouse with cardiac-specific overexpression of H11 kinase (Depre et al. (2002) supra). A line with a 7-fold increase in H11 kinase protein content in the myocardium was used in this analysis; this increase corresponds with in vivo H11 kinase levels during myocardial ischemia (Depre, et al. (2004) *Circ. Res.* 95:433-440). The physiological characteristics of the mouse line are shown in Table 1. The various measured parameters indicate that overexpression of H11 kinase stimulates cardiac cell growth.

TABLE 1

| Parameter | Wild-type (n = 5) | Transgenic n = 5 |
|---|---|---|
| HW/BW (mg/g) | 5.1 ± 0.3 | 7.5 ± 0.5* |
| DSWT (cm) | 0.65 ± 0.04 | 0.85 ± 0.05* |
| SSWT (cm) | 1.0 ± 0.1 | 1.3 ± 0.1* |
| EF (%) | 73 ± 2 | 75 ± 5 |
| HR (per minute) | 398 ± 8 | 409 ± 15 |
| LVSP (mm Hg) | 84 ± 2 | 80 ± 3 |
| LVDP (mm Hg) | 3 ± 1 | 2 ± 1 |
| +dP/dt (mm Hg/sec) | 7625 ± 375 | 8450 ± 519 |

HW, heart weight; BW, body weight; DSWT, end-diastolic septal wall thickness; SSWT, end-systolic septal wall thickness; EF, ejection fraction; HR, heart rate; LVSP, left ventricular end-systolic pressure; LVDP, left ventricular end-diastolic pressure.

To determine whether H11 kinase was cardioprotective in vivo, hearts from both wild-type and transgenic mice were submitted to a ligation of the proximal left anterior descending coronary artery for 20 minutes, 45 minutes or 60 minutes, followed by full reperfusion for 24 hours. The animals were allowed to recover for 24 hours, at which time the hearts were harvested and stained to determine both the area-at-riskarea-at-risk and the infarct size. The infarct size/area-at-riskarea-at-risk ratio was measured by Alcian blue and TTC staining, respectively, in hearts from wild-type and transgenic mice submitted to different durations of no-flow ischemia (n≧4 per group). while the area-at-riskarea-at-risk was similar between both groups, there was a significant reduction of the infarct size/area-at-riskarea-at-risk ratio (P<0.05) in mice overexpressing H11 kinase compared to control littermates at all time points measured. For example, in mice with 45 minute occlusion and 24 hour reperfusion, the infarct size as a fraction of the area-at-risk was 55±5% in wild-type and 10±1% in transgenic mice, respectively (P<0.01), reflecting an 82% reduction in infarct size.

Cardioprotection conferred by H11 kinase was compared to ischemic preconditioning, the most powerful mechanism of protection against ischemic injury described to date. Hearts were preconditioned by six episodes of 4 minutes left anterior descending occlusion and 4 minutes of reperfusion, before a sustained ischemia of 45 minutes. Non-preconditioned controls were submitted to 45 minutes ischemia only. After preconditioning, the infarct size/area-at-risk ratio in wild-type mice was 9±2%, which is an 84% reduction compared to the non-preconditioned wild-type (infarct size/area-at-risk ratio: 55±5%) and is similar to the infarct size/area-at-risk ratio observed without preconditioning in the transgenic mouse (infarct size/area-at-risk ratio: 10±1%). Therefore, the cardioprotection conferred by H11 kinase is quantitatively comparable to the protection of preconditioning. Similar results were found in mice obtained from a different founder with a similar level of H11 kinase overexpression.

To determine whether this protection against necrosis extends to apoptosis, hearts submitted to ischemia/reperfusion were stained for TUNEL analysis. The percentage of apoptotic myocytes was measured specifically in the non-infarcted area-at-risk. There was no difference in apoptosis between wild-type and transgenic sham animals (0.03±0.01% versus 0.04±0.01% TUNEL-positive myocytes). After ischemia/reperfusion, the percentage of TUNEL-positive myocytes increased to 1.3±0.2% in wild-type mice and only to 0.5±0.2% in transgenic mice (P=0.01). Decreased apoptosis in transgenic mice was confirmed by a reduction of DNA fragmentation compared to wild-type.

It has been shown that ischemia/reperfusion rapidly activates a gene program of cardiac cell survival (Depre et al. (2001) supra), including increased phosphorylation of Akt (Depre, et al. (2002) supra). The main pathway activating Akt depends on phosphatidylinositol-3-kinase (PI3K), which can be inhibited by wortmannin. Therefore, it was determined whether the overexpression of H11 kinase is sufficient to trigger such a program. The main mechanisms of cytoprotection previously illustrated include the stimulation of growth/survival signaling pathways and the activation of heat-shock proteins and proto-oncogenes. These mechanisms of survival were tested herein in the transgenic mouse. Phosphorylation of Akt was found to be significantly increased in transgenic mice versus wild-type mice in absence of wortmannin (FIG. 1). After administration of wortmannin, phospho-Akt was almost undetectable in both groups, whereas the expression of total Akt was comparable among all groups. Treatment with wortmannin did not affect the expression of H11 kinase in either wild-type or transgenic mice.

The activation of Akt in transgenic mice was further confirmed by measuring the phosphorylation state of its downstream substrates. Activation of Akt promotes cell survival through the phosphorylation of several downstream effectors, including GSK-3β, Bad, the endothelial isoform of nitric oxide synthase (eNOS) and the transcription factor Foxo (Cantley (2002) surpa). Akt inhibits GSK-3β, an activator of cell death, and also inhibits the pro-apoptotic effector Bad. Reciprocally, Akt activates the cytoprotective eNOS. The phosphorylation of these three substrates at Akt-specific sites was increased in the transgenic mouse compared to wild-type mice. In the nucleus, Akt phosphorylates the pro-apoptotic transcription factors of the Foxo family, which is followed by their inhibition (Cantley (2002) supra). Phosphorylation of Foxo 1a was also increased in transgenic mice compared to wild-type. Inhibition of Foxo by Akt increases the expression of heat-shock proteins (HSPs). Expression of HSP70 and HSP27 was significantly increased in protein extracts from transgenic mice compared to wild-type mice. HSP70, for instance, was increased more than ~6-fold (P<0.01), whereas HSP27 was increased nearly 4-fold (P<0.01). Subcellular fractionation showed both an accumulation of HSPs in the nuclear fraction and a band shift compatible with increased phosphorylation, which both characterize the active proteins (Knowlton (1999) *J. Mol. Cell. Cardiol.* 31:523-532).

Another major mechanism of cardioprotection, activated downstream PI3K, is PKCε (Tong, et al. (2000) *Circ Res.* 87:309-315), Therefore, the potential regulation of PKCε was tested in the transgenic H11 kinase model. Transgenic mice were characterized by a translocation of the enzyme from the soluble to the particulate fraction that was blocked by wortmannin, showing that it relies on a PI3K-dependent mechanism. The activity of PKCε was increased by 40% in transgenic versus wild-type mice. One of the protective mechanisms of PKCε in the heart is to trigger the expression of the inducible isoform of NOS (iNOS), which is particularly important in activating the delayed mechanisms of myocardial protection following ischemia/reperfusion (Bolli (2001) *J. Mol. Cell. Cardiol.* 33:1897-1918). Expression of iNOS protein was increased five-fold in transgenic mice compared to wild-type mice.

It was also determined whether this activation of the PI3K pathway in transgenic mice was necessary for the cardioprotection by H11 kinase. When wortmannin-treated hearts were submitted to a protocol of ischemia/reperfusion, the protection against apoptosis found in hearts from transgenic mice was totally abolished.

H11 kinase overexpression activates glucose metabolism in hearts from transgenic rice (Wang, et al. (2004) supra). Increased reliance upon glucose represents a metabolic survival response to ischemia (Depre, et al. (1999) supra), which is complementary to the anti-apoptotic mechanisms described above. The major regulator of glucose utilization in the ischemic heart is AMPK, which is activated by phosphorylation of its α catalytic subunit (Russell, et al. (2004) supra). Therefore, it was determined whether increased expression of H11 kinase regulates the activity of AMPK. The total and phosphorylated forms of α1AMPK subunit were measured in wild-type and transgenic mice. The expression of total αAMPK was similar between both groups, whereas T(P)172 αAMPK was increased two-fold in transgenic versus wild-type (P<0.05). This increased phosphorylation resulted in a 2-fold increase in AMPK activity. The activation of AMPK in cell culture was further characterized. Isolated cardiac myocytes were infected with an adenovirus harboring the H11 kinase sequence or a β-gal control in a serum-free medium. Whereas β-gal did not affect α1AMPK phosphorylation compared to control cells, addition of H11 kinase significantly increased T(P)172 AMPK by 2-fold (P<0.01 vs. corresponding sham). Expression of α1AMPK was comparable between groups. Increased phosphorylation of both Akt and AMPK after H11 kinase overexpression in isolated myocytes confirms the specificity of the effects observed in the transgenic mouse.

Because H11 kinase belongs to the family of small heat-shock proteins (Smith, et al. (2000) supra), it was determined whether H11 kinase interacts with the survival kinases. Immunoprecipitation of Akt and H11 kinase, or AMPK and H11 kinase, and western blot with the reciprocal antibody showed a signal at the expected size. The specificity of this interaction was confirmed using the hemagglutinin antibody binding only the transgenic protein. To further demonstrate the interaction, a recombinant His-tagged H11 kinase was expressed in *E. coli* and purified by ion exchange chromatography. Co-immunoprecipitation of this purified protein with a Myc-tagged Akt showed a band of the same size as the loading control. The reciprocal experiment, in which a purified His-tagged Akt was co-immunoprecipitated with a Myc-tagged H11 kinase also showed a band of the expected size. No signal was detected after immunoprecipitation with an irrelevant (hemagglutinin) antibody.

Figure 2A:
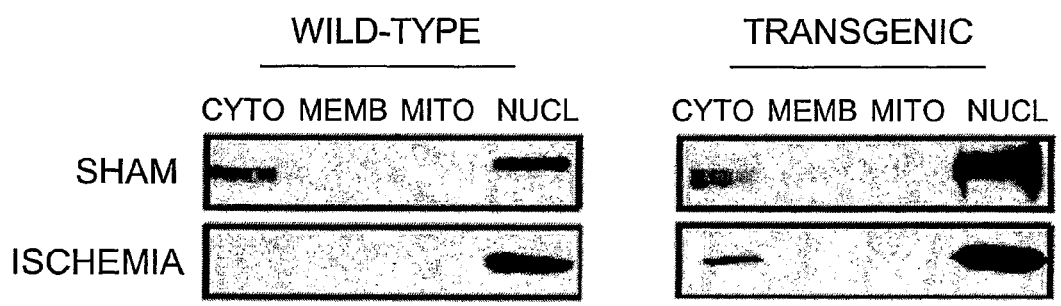
FIG. 2A, subcellular localization of H11 kinase in heart from wild-type and transgenic mice, both in normal conditions and after 45 minutes ischemia. Correct separation of the cytosolic and nuclear fractions was confirmed by Immunoblotting of glucose-6-phosphate dehydrogenase and EGR-1.

Akt and AMPK have antagonistic effects on cardiac cell growth (Hay and Sonenberg (2004) supra), but they are complementary in promoting cardiac cell survival. Thus, it was determined whether these respective effects could be related to a different subcellular distribution. In hearts from wild-type mice, H11 kinase was found in both the nuclear and cytosolic fractions, whereas the overexpressed protein accumulated predominantly in the nuclear fraction of transgenic mice (FIG. 2A). After normalization, H11 kinase was increased 3-fold in the cytosolic fraction and 6-fold in the nuclear fraction of transgenic mice compared to wild-type mice. A preferential localization of the protein in the nucleus was confirmed by immunofluorescence. Using hearts from wild-type mice, it was determined whether this subcellular distribution was affected by ischemia/reperfusion. After 45 minutes of ischemia, the H11 kinase protein content increased by 50% in the nuclear fraction, and this increase persisted up to 24 hours after reperfusion. To test whether this distribution applied to other models of ischemia in vivo, the subcellular distribution of H11 kinase was analyzed in the swine heart submitted to repetitive ischemia, a model in which H11 kinase protein expression increases by 6-fold (Depre, et al. (2004) supra). In this model, H11 kinase was also found in the nuclear fraction, where its expression markedly increased after six episodes of ischemia/reperfusion (FIG. 2B).

In dog heart, subjected to chronic pressure overload, the nuclear expression of H11 kinase increased significantly (FIG. 2C) over control animals. Similarly, in human heart (FIG. 2D), the expression of H11 kinase was found to be nuclear-specific and, as is known in the art, H11 kinase expression increases in patients with ischemic heart disease.

These data demonstrate that in all cases, both in rodents and in larger mammals, the net effect of stress is to increase the nuclear/cytosolic ratio of H11 kinase.

Because of its role in cell death and survival, H11 kinase protein expression was analyzed in melanoma cells. H11 kinase expressed in melanoma cells has been shown to have a Trp$^{51}$→Cys missense mutation (FIG. 3) which dramatically affects the structure of the protein by adding seven supplementary beta-sheets (Gober, et al. (2003) supra). Specifically, the addition of a cysteine creates the possibility of novel disulfide bridges. This mutation induces hyperphosphorylation of H11 kinase. To determine whether this mutation also hyperactivates H11 kinase thereby affecting the subcellular distribution of H11 kinase, localization was detected by immunofluorescence in G-631 melanoma cells. H11 kinase expression was mainly detected in specific areas in the nucleus, which are compatible with stress granules. Counter-staining with DAPI and overlay confirmed that the expression is mainly nuclear. Therefore, this data indicates that this mutation of H11 kinase promotes the nuclear accumulation of the protein and hence, increases the nuclear transfer of Akt. As a consequence, the hyperactivity of growth and survival mechanisms triggers cell transformation.

Considering the protein interactions disclosed herein, it was determined whether the nuclear accumulation of H11 kinase in transgenic mice was associated with a redistribution of Akt and AMPK. The expression of Akt in the nuclear fraction was 4- to 5-fold higher in transgenic mice compared to wild-type mice. Further, the nuclear Akt was active, as shown by its phosphorylation on both Thr$^{308}$ and Ser$^{473}$ in hearts from wild-type and transgenic mice (n=4 per group). Similarly, in wild-type mice, the nuclear/cytosolic ratio of AMPK was 1.7±0.3, whereas this ratio increased to 3.9±0.3 in transgenic mice. These same experiments were repeated with immunoprecipitation carried out separately for cytosolic and nuclear fractions to determine whether the interaction between H11 kinase and the survival kinases was specific for a subcellular compartment. The interaction of H11 kinase with Akt was found in both cytosolic and nuclear fractions, although it largely predominated in the latter. The interaction of H11 kinase with AMPK was detected exclusively in the nuclear fraction. As a result, the transgenic mice were characterized by an increased interaction between Akt and AMPK specifically in the nucleus.

The mechanism by which H11 kinase was translocated was determined. Two consensus sites for sumoylation (ΨKXE; Rodriguez, et al. (2001) *J. Biol. Chem.* 276:12654-12659) were identified in the amino acid sequence for H11 kinase. Immunoprecipitation experiments confirmed that H11 kinase interacts with SUMO, both in wild-type and transgenic mice and this interaction was found specifically in the nuclear fraction. Specificity, of the signal was confirmed by immunoblotting with the hemagglutinin tag of the transgenic protein. Therefore, H11 kinase acts as a nuclear shuttle for Akt through sumoylation.

Both the AMPK and Akt pathways stabilize the hypoxia-inducible transcription factor 1α (HIF-1α) (Lee, et al. (2003) *J. Biol. Chem.* 278:39653-39661; Kim, et al. (2002) *Circ. Res.* 90:25e-33), which is essential in the transcriptional adaptation of the cell to oxygen deprivation. HIF-1α expression was increased by more than 5-fold in nuclear fractions from hearts of transgenic mice compared to wild-type mice. Activation of HIF-1α results in an increased expression of genes encoding enzymes regulating anaerobic metabolism and growth factors (Semenza (2001) *Cell* 107:1-4). To test this genomic effect, cDNA from hearts of wild-type and transgenic mice were hybridized to mouse-specific micro-arrays. The transgenic mouse heart was characterized by an upregulation of multiple genes regulated by HIF-1α and involved in glycogen metabolism, glycolysis and glucose oxidation (Table 2). The profile includes a marked upregulation of 6-Phospho-2-fructokinase (PFK-2), the enzyme responsible for the production of fructose 2,6-bisphosphate (Fru-2,6-bis P), the most powerful activator of glycolysis in the heart (Depre, et al. (1993) *J. Biol. Chem.* 268:13274-13279). To determine the biological relevance of this increased expression of PFK-2, the concentration of Fru-2,6-bis P was measured. Fru-2,5-bis P was increased two-fold in hearts from transgenic mice compared to wild-type mice. In addition, expression of other survival genes activated by HIF-1α was also increased (Table 2).

TABLE 2

| Function | Gene | Ratio | P value |
| --- | --- | --- | --- |
| Glycogenolysis | Phosphorylase kinase alpha | 1.5 | 0.02 |
| Glycogenolysis | Phosphorylase kinase gamma | 1.8 | 0.003 |
| Glycogenolysis | Muscle glycogen Phosphorylase | 1.3 | 0.02 |
| Glycogenolysis | Glycogen synthase | 2.1 | 0.04 |
| Glycogenolysis | UDP-glucose Pyrophosphorylase | 2.1 | 0.02 |
| Glycogenolysis | Amylo-1,6-glucosidase | 1.8 | 0.02 |
| Glycogenolysis | Phosphoglucomutase | 1.6 | 0.02 |
| Glycolysis | Hexokinase | 1.7 | 0.0001 |
| Glycolysis | Phosphofructokinase, muscle | 1.8 | 0.01 |
| Glycolysis | 6-PFK-2/FBPase-2, isoforms 2 | 3.9 | 0.0006 |
| Glycolysis | 6-PFK-2/FBPase-2, isoforms 1 | 2.3 | 0.001 |
| Glycolysis | Aldolase | 11.0 | 0.0001 |
| Glycolysis | Phosphoglycerate kinase 2 | 5.7 | 0.001 |
| Glycolysis | Enolase 3, beta muscle | 1.5 | 0.005 |

TABLE 2-continued

| Function | Gene | Ratio | P value |
| --- | --- | --- | --- |
| Glycolysis | Lactate dehydrogenase B | 1.7 | 0.001 |
| Oxidation | PDH kinase 2 | 1.6 | 0.01 |
| Oxidation | PDH E1 alpha | 1.7 | 0.03 |
| Oxidation | PDH (lipoamide) beta | 1.5 | 0.006 |
| Oxidation | PDH phosphatase | 1.2 | 0.04 |
| Survival | VEGF | 2.1 | 0.01 |
| Survival | Heme oxygenase-1 | 1.4 | 0.03 |
| Survival | IGFBP-3 | 1.6 | 0.009 |
| Survival | IGF2 receptor | 2.0 | 0.0006 | n = 4 per group.

To understand the role of the cytosolic protein, adeno-mediated overexpression of H11 kinase was performed in isolated neonatal cardiac myocytes. At low viral doses (3-10 multiplicity of infection; MOI), H11 kinase migrated to the nuclear envelope and could be seen in intranuclear granules. This was accompanied by an increase in phosphorylation of Akt. It has been demonstrated that in this range of virus delivery, the activation of Akt is accompanied by monocyte hypertrophy (Depre, et al. (2002) *Circ. Res.* 91:1007-1014). At higher viral doses (30-100 MOI), however, H11 kinase protein accumulated in the cytosol, most likely because of a saturation of the nuclear translocation system. This cytosolic accumulation of H11 kinase resulted in a dose-dependent increase in conjugation to ubiquitin, with subsequent delivery to the proteasome degradation system. Because of the interaction between H11 kinase and Akt, the targeting of the H11 kinase-Akt complex to ubiquitination and further degradation resulted in a dose-dependent decrease in the cellular content of Akt. This was accompanied by a deactivation of downstream targets of Akt, such as $p70^{S6K}$. As a consequence, cardiac cell apoptosis measured by caspase-3 activity, was activated in a dose-dependent manner. Therefore, a cytosolic accumulation of H11 kinase acts as a tumor suppressor. These results can explain why it has been observed that H11 kinase promotes apoptosis after overexpression of H11 kinase in vitro (Gober, et al. (2003) *J. Biol. Chem.* 278(39):37600-9), and why the cytosolic expression of H11 kinase decreases in conditions of ischemic stress. These data also show that manipulation of H11 kinase expression and subcellular localization can direct the cell into a pathway of cell survival or cell death. Accordingly, manipulating the expression and localization of H11 kinase is useful in the prevention or treatment of heart disease (where survival needs to be promoted) and cancer (where cell death must be enhanced).

Despite its small size, H11 kinase shows a relatively complex structure, including a poly-proline stretch, the different domains characterizing a serine/threonine kinase and a C-terminus crystallin domain. Although the substrate of the kinase is presently unknown, a kinase activity has been demonstrated using the basic myelin protein as generic substrate (Depre et al. (2002) supra). The crystallin domain is very similar to the well-characterized αB-crystallin, hence the name of αC-crystallin for H11 kinase in the mouse (Bany and Schultz (2001) *Biol. Reprod.* 64:284-292) or small heat-shock protein in humans (Kappe et al. (2001) supra; Benndorf et al. (2001) *J. Biol. Chem.* 276:26753-26761). The mechanisms by which H11 kinase promotes cell survival are multifactorial. Instead of being part of a specific signaling pathway, H11 kinase redistributes signaling molecules between different compartments, prevents their deactivation, and promotes their interactions. Several reports have shown that HSP70 overexpression dramatically reduces infarct size both in vivo and in vitro (Radford et al. (1996) *Proc. Natl. Acad.*

Sci. USA. 93:2339-2342; Marber et al. (1995) *J. Clin. Invest.* 95:1446-1456; Mestril et al. (1994) *J. Clin. Invest.* 93:759-767). The small HSP27 (Vander Heide (2002) *Am. J. Physiol. Heart Circ. Physiol.* 282:H935-941) and the cardiac-specific cochaperone mmDJA4 also have anti-apoptotic and cytoprotective effects (Depre et al. (2003) *Cardiovasc. Res.* 58:126-135). The effects of H11 kinase on both cardiac cell growth and survival via activation of Akt was also demonstrated herein. Akt is a major regulator of cell growth and survival, protein synthesis, and metabolism (Cantley (2002) *Science* 296:1655-1657). The associated between H11 kinase and Akt is reminiscent of HSP90, which binds Akt, prolongs its half-life, increases its activity and promotes its membrane localization (Basso, et al. (2002) *J. Biol. Chem.* 277:39858-39866). The Akt/p70$^{S6K}$ pathway is primarily involved in the translational adaptation of the heart (Morisco et al. (2000) *J. Biol. Chem.* 275:14466-14475), which eventually leads to increased cell size in response to cardiac overload (Sugden and Clerk (1998) *J. Mol. Med.* 76:725-746; Sugden (1999) *Circ. Res.* 84:633-646), but the activation of the Akt pathway is also coupled to protective mechanisms that limit the cell loss induced by ischemia/reperfusion injury (Depre et al. (2001) supra; Brar (2002) *J. Mol. Cell. Cardiol.* 34:483-492; Cook et al. (2002) *J. Biol. Chem.* 277:22528-22533; Jonassen et al. (2001) *Circ. Res.* 89:1191-1198; Mehrhof et al. (2001) *Circulation* 104:2088-2094; Matsui et al. (2001) *Circulation* 104:330-335; Gao et al. (2002) *Circulation* 105:1497-1502; Negoro et al. (2001) *Circulation* 103:555-561; Fujio et al. (2000) *Circulation* 101:660-667). Activation of Akt by H11 kinase therefore represents not only a mechanism by which cell growth can be stimulated, but also a mechanism through which cell survival can be promoted. Reciprocal activation by heat-shock proteins and the Akt-mTOR pathway have been described (Xavier et al. (2000) *J. Biol. Chem.* 275:29147-29152; Huang and Bunn (2003) *J. Biol. Chem.* 278:19575-19578; Rane et al. (2003) *J. Biol. Chem.* 278:27828-27835), reinforcing the importance of this axis in the phenotype of the transgenic mouse and in the cardioprotection during ischemia. These mechanisms are very different but complementary, which further demonstrates that H11 kinase acts as a master switch in the cardiac adaptation to stress.

Moreover, concomitant activation of several survival kinases creates important cross talk. Increased activity of PKCε may further activate Akt and the Akt-dependent anti-apoptotic mechanisms. Increased activity of PKCε may also activate AMPK Nishino, et al. (2004) *Cardiovasc. Res.* 61:610-619), which will promote the activation of HIF-1α (Lee, et al. (2003) supra). Increased stability of HIF-1α may also originate from the Akt pathway (Kim, et al. (2002) supra). In addition, both PKCε and HIF-1α can stimulate the expression of iNOS, which is central to the mechanisms of prolonged cardioprotection (Bolli (2001) supra; Jung, et al. (2000) *Circ. Res.* 86:319-325). Increased production of NO stabilizes the HIF-1α protein (Zhou and Brune (2005) *Toxicology* 208:223-233) and increases the activity of PKCε (The 5-fold increase of iNOS expression in our model corresponds to the range found in models of preconditioning and does not induce the deleterious effects resulting from a massive production of NO[20]

H11 kinase is the eukaryotic homologue of the viral protein ICP10 kinase, which confers the immortalization of cells infected by Herpes Simplex type II (Smith et al. (2000) supra). H11 kinase homologues have not been identified in *S. Cerevisae, C. Elegans, D. Melanogaster, D. Rerio* or *G. Gallus*, however, the gene was found in all mammalian species tested, including mouse, rat, swine, dog, sheep, monkey and human. In light of this finding and the relatively rudimentary structure of H11 kinase as compared to other mammalian serine/threonine kinases, mammals may have co-opted the H11 kinase gene from the Herpes Simplex ICP10 protein kinase. Considering the powerful effect of ICP10 protein kinase on cell proliferation, the insertion of H11 kinase in the mammalian genome would represent the addition of a novel mechanism of cell growth and survival. H11 kinase is not the first example of a stress-related protein that is activated by nuclear translocation (Knowlton et al. (2000) supra; Alastalo et al. (2003) *J. Cell Sci.* 116:3557-35; Danen-van Oorschot et al. (2003) *J. Biol. Chem.* 278:27729-27736), however it is a novel example of a protein with diametrically opposite effects depending on its subcellular localization.

Activation of a genomic program of cell survival is found during acute (Depre, et al. (2001) *Proc. Natl. Acad. Sci. USA* 98:9336-9341) and prolonged (Depre, et al. (2004) supra) ischemia. This program is particularly developed in human hibernating myocardium, a condition in which the myocardium submitted to chronic ischemia remains viable and functionally improves upon reperfusion (Depre, et al. (2004) supra). In patients with hibernating myocardium, the genomic program of cell survival includes an upregulation of H11 kinase itself, as well as an increase in cytoprotective (HSP70, GLUT1) and anti-apoptotic genes (inhibitor of apoptosis) (Depre, et al. (2004) supra). Therefore, the mechanisms of cytoprotection activated in human hibernating myocardium and those described in the H11 kinase transgenic mouse seem similar. Because the increase in H11 kinase expression is relatively similar in both conditions, the hibernating heart may be preconditioned, which would be a crucial mechanism to maintain its viability during prolonged ischemia. As a consequence, a pre-emptive overexpression of H11 kinase in ischemic myocardium protects against ischemic damage.

Moreover, H11 kinase not only protects the myocardium against apoptosis, but also promotes the metabolic switch that characterizes the ischemic heart. Glucose uptake and glycolysis are rapidly activated upon ischemia to compensate for the lack of mitochondrial ATP production that results from oxygen deprivation (Depre, et al. (1999) supra). AMPK is essential for this adaptation (Russell, et al. (2004) supra), by promoting the membrane translocation of glucose transporters and by stimulating glycolysis through increased production of Fru-2,6-bis P (Marsin, et al. (2000) supra). Through this metabolic adaptation, AMPK limits apoptosis and irreversible damage (Russell, et al. (2004) supra), which shows that the metabolic and anti-apoptotic mechanisms of cardioprotection are intertwined. This is further supported by the observation that Akt both inhibits pro-apoptotic effectors and stimulates glucose utilization (Cantley (2002) supra). Given that H11 kinase affords cardioprotection and is useful in preventing myocardial infarction, agents which modulate the subcellular localization of H11 kinase H11K can pre-emptively precondition the heart, thereby limiting necrosis and apoptosis during ischemia. Accordingly, the present invention relates to a method for the identification of modulators, e.g., inhibitors, antagonists, or agonists, of H11 kinase activity by detecting the ability of test agents to effect an alteration of H11 kinase subcellular localization (qualitatively and/or quantitatively), and thus, its activity and, hence, cell growth or survival.

An H11 kinase as used herein includes, but is not limited to, any H11 kinase protein, mutant H11 kinase (e.g., Trp$^{51}$→Cys), or derivative, homolog or fragment thereof. An H11 kinase can be of any species, e.g., mouse, rat, swine, dog, sheep, monkey, human, etc. In particular embodiments, an H11 kinase is a human H11 kinase, mutant H11 kinase, or derivative, homolog, or fragment thereof.

In the identification of agents which modulate the localization of H11 kinase and thus cell growth or survival, particularly in the heart, host cells (e.g., heart muscle cells such as cardiac myocytes) which express H11 kinase are contacted with or exposed to at least one test agent at a point of application, such as a well, in a plate containing the test cell and incubated for a time sufficient to allow the test agent to effect localization of H11 kinase.

Alternatively, cells used in accordance with the method of the invention can be brought in contact with and immobilized onto a solid phase support or carrier such as nitrocellulose, glass, polystyrene, or other solid support which is capable of immobilizing cells. The support can then be washed with suitable buffers, contacted with the test agent and subsequently treated with a detectably labeled molecule to determine the localization of H11 kinase.

The cell in which the localization of H11 kinase is detected and/or measured can be in vitro (e.g., isolated in cell culture) or in vivo and can be mammalian, bovine, murine, rat, primate, human, etc. The H11 kinase which is expressed can be mammalian, bovine, murine, rat, canine, primate, human, etc. The cell can be a cell of primary tissue, a cell line, or of an animal containing and expressing a H11 kinase transgene. For example, the transgenic animal can be a mouse. Transgenic animals can be made by standard methods well-known in the art.

In one embodiment of the invention, nucleic acids encoding H11 kinase are endogenously produced by the host cell. In another embodiment, nucleic acids encoding an H11 kinase fragment or derivative are introduced into the host cell for expression of said fragment or derivative. In yet another embodiment, H11 kinase is microinjected into the cell.

H11 kinase, H11 kinase mutants, derivatives, fragments, and analogs to be screened by the assay methods of the invention can be produced by various methods known in the art. The manipulations which result in their production can occur at the gene or protein level. For example, the cloned H11 kinase gene sequences can be modified by any of numerous strategies known in the art (Sambrook et al. (1989) Molecular Cloning, A Laboratory Manual, 2nd Ed., Cold Spring Harbor Laboratory Press, Cold Spring Harbor, N.Y.). The sequences can be cleaved at appropriate sites with restriction endonuclease(s), followed by further enzymatic modification if desired, isolated, and ligated in vitro. In the production of the gene encoding a derivative, homolog or analog of H11 kinase, care should be taken to ensure that the modified gene retains the original translational reading frame, uninterrupted by translational stop signals, in the gene region where the desired activity is encoded.

Additionally, the H11 kinase-encoding nucleic acid sequence can be mutated in vitro or in vivo, to create and/or destroy translation, initiation, and/or termination sequences, or to create variations in coding regions and/or form new restriction endonuclease sites or destroy pre-existing ones, to facilitate further in vitro modification. Any technique for mutagenesis known in the art can be used including, but not limited to, chemical mutagenesis and in vitro site-directed mutagenesis (Hutchinson et al. (1978) *J. Biol. Chem.* 253: 6551-6558), amplification with PCR primers containing a mutation, etc.

H11 kinase fragments or derivatives, whether produced by recombinant DNA techniques, chemical synthesis methods, or by purification from native sources include, but are not limited to, those containing, as a primary amino acid sequence, all or part of the amino acid sequences substantially as provided in SEQ ID NO:1, as well as fragments and other analogs and derivatives thereof, including proteins homologous thereto.

Manipulations of H11 kinase sequences can be made at the protein level. Included within the scope of the invention is a H11 kinase fragment, derivative or analog that is differentially modified during or after translation, e.g., by glycosylation, acetylation, phosphorylation, amidation, derivatization, sumoylation by known protecting/blocking groups, proteolytic cleavage, linkage to an antibody molecule or other cellular ligand, etc. Any of numerous chemical modifications can be carried out by known techniques including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.

H11 kinase amino acid sequences can also be modified to include a fluorescent label. Alternatively, H11 kinase is modified to have a heterofunctional reagent; such heterofunctional reagents can be used to crosslink H11 kinase to other proteins.

In addition, analogs and derivatives of H11 kinase can be chemically synthesized. For example, a peptide corresponding to a portion of H11 kinase, which comprises a desired domain or mediates a desired activity in vitro, can be synthesized by use of a peptide synthesizer. Furthermore, if desired, non-classical amino acids or chemical amino acid analogs can be introduced as a substitution or addition into the H11 kinase protein. Non-classical amino acids include, but are not limited to, the D-isomers of the common amino acids, α-amino isobutyric acid, 4-aminobutyric acid (4-Abu), 2-aminobutyric acid (2-Abu), 6-amino hexanoic acid (Ahx), 2-amino isobutyric acid (2-Aib), 3-amino propionoic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In particular, H11 kinase derivatives can be made by altering their sequences by substitutions, additions or deletions that provide for functionally equivalent molecules. Due to the degeneracy of nucleotide coding sequences, other DNA sequences that encode substantially the same amino acid sequence as a H11 kinase gene or cDNA can be used in the practice of the present invention. These include, but are not limited to, nucleotide sequences encoding all or portions of the H11 kinase that are altered by the substitution of different codons that encode a functionally equivalent amino acid residue within the sequence, thus producing a silent change. For example, one or more amino acid residues within the sequence can be substituted by another amino acid of a similar polarity that acts as a functional equivalent, resulting in a silent alteration. Substitutes for an amino acid within the sequence can be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The H11 kinase derivatives and analogs can be analyzed by hydrophilicity analysis (Hopp and Woods (1981) *Proc. Natl. Acad. Sci. USA* 78:3824-3828). A hydrophilicity profile can be used to identify the hydrophobic and hydrophilic regions of the proteins, and help predict their orientation in designing substrates for experimental manipulation, such as in binding experiments, antibody synthesis, etc. Secondary structural analysis can also be performed to identify regions of H11 kinase, or derivatives thereof, that assume specific structures (Chou and Fasman (1974) *Biochemistry* 13:222-23). Manipulation, translation, secondary structure prediction, hydrophilicity and hydrophobicity profile predictions, open reading frame prediction and plotting, and determination of sequence homologies, etc., can be accomplished using computer software programs available in the art.

Other methods of structural analysis including, but not limited to, X-ray crystallography (Engstrom (1974) *Biochem. Exp. Biol.* 11:7-13), mass spectroscopy and gas chromatography (Methods in Protein Science, J. Wiley and Sons, N.Y., 1997), and computer modeling (Fletterick and Zoller, eds., 1986, Computer Graphics and Molecular Modeling, In: Current Communications in Molecular Biology, Cold Spring Harbor Laboratory, Cold Spring Harbor Press, NY) can also be employed to determine which residues to modify in producing a fragment or derivative or analog of a H11 kinase.

Methods for recombinant production of H11 kinase and derivatives or fragments or homologs thereof for use in the screening methods of the present invention are well-known to those skilled in the art. Nucleic acids encoding H11 kinase, derivatives, fragments, and homologs thereof are known in the art and can readily be obtained from databases such as EMBL and GENBANK (see, e.g., accession numbers BT006876, AF525493, and AF133207). The nucleotide sequences encoding illustrative human and mouse H11 kinase are known and are provided as SEQ ID NO:2 and SEQ ID NO:3, respectively. Nucleic acids encoding H11 kinase can be obtained by any method known in the art, e.g., by PCR amplification using synthetic primers hybridizable to the 3' and 5' ends of each sequence, and/or by cloning from a cDNA or genomic library using an oligonucleotide specific for each nucleotide sequence.

Homologs (e.g., nucleic acids encoding H11 kinase of species other than human) or other related sequences (e.g., paralogs) can be obtained by low, moderate or high stringency hybridization with all or a portion of the particular human sequence as a probe, using methods well-known in the art for nucleic acid hybridization and cloning.

An encoded H11 kinase protein, which is depicted as SEQ ID NO:1 can be obtained by methods well-known in the art for protein purification and recombinant protein expression. For recombinant expression H11 kinase, the nucleic acid containing all or a portion of the nucleotide sequence encoding the protein can be inserted into an appropriate expression vector, i.e., a vector that contains the necessary elements for the transcription and translation of the inserted protein coding sequence. The necessary transcriptional and translational signals can also be supplied by the native promoter of the H11 kinase gene, and/or its flanking regions.

A variety of host-vector systems can be utilized to express the protein coding sequence. These include, but are not limited to, mammalian cell systems infected with virus (e.g., vaccinia virus, adenovirus, etc.); insect cell systems infected with virus (e.g., baculovirus); microorganisms such as yeast containing yeast vectors; or bacteria transformed with bacteriophage, DNA, plasmid DNA, or cosmid DNA. The expression elements of vectors vary in their strengths and specificities. Depending on the host-vector system utilized, any one of a number of suitable transcription and translation elements can be used.

Any method available in the art can be used for the insertion of DNA fragments into a vector to construct expression vectors containing a chimeric gene consisting of appropriate transcriptional/translational control signals and protein coding sequences. These methods can include in vitro recombinant DNA and synthetic techniques and in vivo recombinant techniques (genetic recombination). Expression of nucleic acid sequences encoding H11 kinase, or a derivative, fragment or homolog thereof, can be regulated by a second nucleic acid sequence so that the gene or fragment thereof is expressed in a host transformed with the recombinant DNA molecule(s). For example, expression of the protein can be controlled by any promoter/enhancer known in the art. Further, the promoter may not be native to the gene for H11 kinase. Promoters that can be used include, but are not limited to, the SV40 early promoter (Bernoist and Chambon (1981) *Nature* 290:304-310), the promoter contained in the 3' long terminal repeat of Rous sarcoma virus (Yamamoto et al. (1980) *Cell* 22:787-797), the herpes thymidine kinase promoter (Wagner et al. (1981) *Proc. Natl. Acad. Sci. USA* 78:1441-1445), the regulatory sequences of the metallothionein gene (Brinster et al. (1982) *Nature* 296:39-42); prokaryotic expression vectors such as the β-lactamase promoter (VIIIa-Kamaroff et al. (1978) *Proc. Natl. Acad. Sci. USA* 75:3727-3731) or the tac promoter (DeBoer et al. (1983) *Proc. Natl. Acad. Sci. USA* 80:21-25; Gilbert et al. (1980) *Scientific American* 242:79-94); plant expression vectors comprising the nopaline synthetase promoter (Herrar-Estrella et al. (1984) *Nature* 303:209-213) or the cauliflower mosaic virus 35S RNA promoter (Garder et al. (1981) *Nucleic Acids Res.* 9:2871), and the promoter of the photosynthetic enzyme ribulose bisphosphate carboxylase (Herrera-Estrella et al. (1984) *Nature* 310:115-120); promoter elements from yeast and other fungi such as the Gal4 promoter (Johnston et al. (1987) *Microbiol. Rev.* 51:458-476), the alcohol dehydrogenase promoter (Schibler et al. (1987) *Ann. Rev. Genet.* 21:237-257), the phosphoglycerol kinase promoter (Struhl et al. (1995) *Ann. Rev. Genet.* 29:651-674-257; Guarente (1987) *Ann. Rev. Genet.* 21:425-452), the alkaline phosphatase promoter (Struhl et al. (1995) *Ann. Rev. Genet.* 29:651-674-257; Guarente (1987) *Ann. Rev. Genet.* 21:425-452), and animal transcriptional control regions that exhibit tissue specificity and have been utilized in transgenic animals include alpha-myosin heavy chain promoter (Sanbe et al. (2003) *Circ. Res.* 92(6):609-16) or alpha-MHC (Kirchhefer, et al. (2003) *Cardiovasc. Res.* 59(2):369-79).

In general, a vector is used that contains a promoter operably linked to the nucleic acid sequence encoding H11 kinase, or a fragment, derivative or homolog thereof, one or more origins of replication, and optionally, one or more selectable markers (e.g., an antibiotic resistance gene).

An expression vector containing the coding sequence, or a portion thereof, of H11 kinase can be made by subcloning the gene sequence into the EcoRI restriction site of each of the three pGEX vectors (glutathione S-transferase expression vectors; Smith and Johnson (1988) *Gene* 7:31-40). This allows for the expression of products in the correct reading frame.

Expression vectors containing the sequences of interest can be identified by three general approaches: (a) nucleic acid hybridization, (b) presence or absence of marker gene function, or (c) expression of the inserted sequences. In the first approach, H11 kinase sequences can be detected by nucleic acid hybridization to probes containing sequences homologous and complementary to the inserted sequences. In the second approach, the recombinant vector/host system can be identified and selected based upon the presence or absence of certain marker functions (e.g., resistance to antibiotics, occlusion body formation in baculovirus, etc.) caused by insertion of the sequences of interest in the vector. For example, if an H11 kinase gene, or portion thereof, is inserted within the marker gene sequence of the vector, recombinants containing the H11 kinase fragment will be identified by the absence of the marker gene function (e.g., loss of beta-galactosidase activity). In the third approach, recombinant expression vectors can be identified by assaying for the H11 kinase expressed by the recombinant vector.

Once recombinant H11 kinase expression vectors are identified and isolated, several methods known in the art can be used to propagate them. Using a suitable host system and growth conditions, recombinant expression vectors can be propagated and amplified in quantity. Expression vectors or derivatives which can be used include, but are not limited to, human or animal viruses such as vaccinia virus or adenovirus; insect viruses such as baculovirus, yeast vectors; bacteriophage vectors such as lambda phage; and plasmid and cosmid vectors.

In addition, a host cell strain can be chosen that modulates the expression of the inserted sequences, or modifies or processes the expressed proteins in the specific fashion desired. Expression from certain promoters can be elevated in the presence of certain inducers; thus expression of the genetically-engineered H11 kinase can be controlled. Furthermore, different host cells have characteristic and specific mechanisms for the translational and post-translational processing and modification (e.g., glycosylation, phosphorylation, etc.) of proteins. Appropriate cell lines or host systems can be chosen to ensure that the desired modification and processing of the foreign protein is achieved. For example, expression in a bacterial system can be used to produce an unglycosylated core protein, while expression in mammalian cells ensures native glycosylation of a heterologous protein. Furthermore, different vector/host expression systems can effect processing reactions to different extents.

An H11 kinase protein or a fragment, homolog or derivative thereof, can be expressed as fusion or chimeric protein products comprising the protein, fragment, homolog, or derivative joined via a peptide bond to a heterologous protein sequence of a different protein. Such chimeric products can be made by ligating the appropriate nucleic acid sequences encoding the desired amino acids to each other by methods known in the art, in the proper coding frame, and expressing the chimeric products in a suitable host by methods commonly known in the art. Alternatively, such a chimeric product can be made by protein synthetic techniques, e.g., by use of a peptide synthesizer. Chimeric genes containing portions of H11 kinase fused to any heterologous protein-encoding sequences can be constructed.

Methods that can be used to carry out the foregoing are commonly known in the art. The cells used in the methods of this embodiment of the invention can either endogenously or recombinantly express H11 kinase, or a fragment, derivative or analog thereof. Recombinant expression of H11 kinase is carried out by introducing H11 kinase encoding nucleic acids into expression vectors and subsequently introducing the vectors into a cell to express H11 kinase or simply introducing H11 kinase encoding nucleic acids into a cell for expression using procedures well-known in the art (e.g., microinjection, liposome-mediated transfection, electroporation, or calcium phosphate precipitation). Nucleic acids encoding H11 kinase from a number of species have been cloned and sequenced and their expression is well-known in the art. Illustrative examples of H11 kinase are set forth in SEQ ID NO:1. Expression can be from expression vectors or intrachromosomal, as is known in the art. See, e.g., Molecular Biology, Ausubel, F. M. et al. (eds.) Greene Publishing Associates, (1989), and other standard laboratory manuals.

Agents which modulate the localization of H11 kinase can be rationally designed from the crystal structure of the protein of interest or identified from a library of test agents. Test agents of a library can be synthetic or natural compounds. A library can comprise either collections of pure agents or collections of agent mixtures Examples of pure agents include, but are not limited to, peptides, polypeptides, antibodies, oligonucleotides, carbohydrates, fatty acids, steroids, purines, pyrimidines, lipids, synthetic or semi-synthetic chemicals, and purified natural products, derivatives, structural analogs or combinations thereof. Examples of agent mixtures include, but are not limited to, extracts of prokaryotic or eukaryotic cells and tissues, as well as fermentation broths and cell or tissue culture supernatants. In the case of agent mixtures, one may not only identify those crude mixtures that possess the desired activity, but also monitor purification of the active component from the mixture for characterization and development as a therapeutic drug. In particular, the mixture so identified can be sequentially fractionated by methods commonly known to those skilled in the art which may include, but are not limited to, precipitation, centrifugation, filtration, ultrafiltration, selective digestion, extraction, chromatography, electrophoresis or complex formation. Each resulting subfraction can be assayed for the desired activity using the original assay until a pure, biologically active agent is obtained.

Agents of interest in the present invention are those with functional groups necessary for structural interaction with proteins, particularly hydrogen bonding, and typically include at least an amine, carbonyl, hydroxyl or carboxyl group. The agents often comprise cyclical carbon or heterocyclic structures and/or aromatic or polyaromatic structures substituted with one or more of the above functional groups.

Subsequent to applying the test agent to the host cells containing H11 kinase, the subcellular localization of H11 kinase is determined. Any method known in the art for determining or measuring the subcellular localization of H11 kinase, i.e., nuclear or cytosolic localization, can be used in the present invention. For example, and not by way of limitation, one such method of detection is contacting a cell with an antibody specific for H11 kinase, detecting the antibody binding present in the nucleus and cytosol, correlating the amount of antibody present with the amount of H11 kinase present thereby determining the ratio of nuclear versus cytosolic-localized H11 kinase. A particular method of detecting H11 kinase subcellular localization is to contact a labeled anti-H11 kinase antibody, e.g., labeled with a fluorescent dye, to whole cells, which can be permeabilized, and then to detect the localization of the label in the cell by, e.g., laser scanning microscopy, immunofluorescence, or immunoelectron microscopy for in situ detection of the H11 kinase.

In situ detection can be accomplished by contacting a cell endogenously or recombinantly expressing a H11 kinase with a labeled molecule that binds to H11 kinase and detecting any binding that occurs and that is localized to the nucleus or cytosol. Alternatively, an unlabeled molecule can be used, in combination with a labeled binding partner of the molecule. Using such an assay, it is possible to determine not only the presence of the H11 kinase, but also its subcellular distribution, i.e., in the nucleus or cytosol.

As another alternative, a substrate-based assay can be conducted to determine the amount of H11 kinase present in a subcellular compartment.

Alternatively, H11 kinase can be labeled with a fluorescent tag (e.g., tagged with GFP or a biotin peptide) and localization can be ascertained by fluorescent microscopy. When fluorescently labeled, the amount of H11 kinase in any particular subcellular compartment is directly proportional to fluorescence intensity.

Another method of detecting and/or measuring H11 kinase subcellular localization is to isolate nuclei from cytosolic preparations using standard methodologies and detect the amount of H11 kinase present in the nucleus and the cytosol. Isolation of the nucleus and the cytosol can be accomplished by, e.g., density gradient centrifugation. After isolation of the nucleus and cytosol, detection of H11 kinase can be accomplished, e.g., by immunoprecipitating H11 kinase with an anti-H11 kinase antibody or binding to anti-H11 kinase antibody on an immunoaffinity column or immobilized on a plate or in a well, or visualizing the protein by western blot analysis. Again, the amount of H11 kinase in any particular subcellular compartment is directly proportional to the amount of bound antibody. General methods for detecting and/or quantitating antigens are well-known in the art (see, for example, Harlow and Lane (1988) supra). Such well-known immunoassays include antibody capture assays, antigen capture assays, and two-antibody sandwich assays.

In another embodiment of the invention, H11 kinase localization to the nucleus or cytosol can be detected and/or measured by isolating nuclei and cytosol, separating proteins therein on a SDS-PAGE gel, eluting separated H11 kinase protein from the gel, and subjecting the eluted H11 kinase to mass spectroscopy analysis for sequence analysis. Such mass spectroscopy analysis can be carried out by any suitable method of mass spectroscopy known in the art, e.g., the method described in Neubauer et al. (1998) *Nature Genetics* 20:46-50; Neubauer et al. (1997) *Proc. Natl. Acad. Sci. USA* 94:385-390; and Wilm et al. (1996) *Nature* 379:466-469.

Those skilled in the art will be able to determine operative and optimal assay conditions for each determination by employing routine experimentation.

Further, isoform-specific agents can be generated which specifically bind to and inhibit the activity of a mutant form of H11 kinase (e.g., a $Trp^{51} \rightarrow Cys$ mutant). As will be appreciated by one of skill in the art, structural analysis of the mutant H11 kinase can provide peptidomimetics and other lead compounds. A potential analog can be examined through the use of computer modeling using a docking program such as GRAM, DOCK, or AUTODOCK. This procedure can include computer fitting of potential analogs. Computer programs also can be employed to estimate the attraction, repulsion, and steric hindrance of an analog to a potential binding site. Generally the tighter the fit (e.g., the lower the steric hindrance, and/or the greater the attractive force) the more potent the potential analog will be since these properties are consistent with a tighter binding constant. Furthermore, the more specificity in the design of a potential analog the more likely that the analog will not interfere with the activity of a mutant H11 kinase. This will minimize potential side-effects due to unwanted interactions with other proteins.

Initially a potential analog could be obtained by screening a random peptide library produced by a recombinant bacteriophage, for example, or a chemical library. An analog ligand selected in this manner could then be systematically modified by computer modeling programs until one or more promising potential ligands are identified.

Such computer modeling allows the selection of a finite number of rational chemical modifications, as opposed to the countless number of essentially random chemical modifications that could be made, and of which any one might lead to a useful agent. Thus, the three-dimensional structure and computer modeling, provides that a large number of agents can be rapidly screened and a few likely candidates can be determined without the laborious synthesis of untold numbers of agents.

Antibodies or antibody fragments directed against H11 kinase for use in detecting H11 kinase can be prepared using standard methods. Accordingly, an H11 kinase protein, fragment or analog or derivative thereof, in particular, a human H11 kinase protein or fragment thereof, can be used as immunogen to generate anti-H11 kinase protein antibodies. Such antibodies can be polyclonal, monoclonal, chimeric, single chain, Fab fragments, or from an Fab expression library. Methods for the production of such antibodies are well-known in the art (see, e.g., Kohler and Milstein (1975) *Nature* 256:495-497; Gustafsson et al. (1991) *Hum. Antibodies Hybridomas* 2:26-32; Kozbor et al. (1983) *Immunology Today* 4:72; Cole et al. (1985) In: Monoclonal Antibodies and Cancer Therapy, Alan R. Liss, Inc., pp. 77-96).

An antibody specific for H11 kinase can be used in methods known in the art, and those methods disclosed herein, relating to the localization and/or quantification of H11 kinase proteins of the invention, e.g., for imaging these proteins, measuring levels thereof in appropriate physiological samples, in diagnostic methods, etc.

As disclosed herein, H11 kinase has opposing activities depending on its subcellular localization. Both qualitative (a difference in localization of H11 kinase) and quantitative (a difference in the amount of H11 kinase localized to a particular location such as the nucleus or cytosol) changes in H11 kinase may be detected and/or measured in accordance with the present invention. Thus, the screening method further involves determining the net ratio of nuclear-localized versus cytosolic-localized H11 kinase is determined in a first cell which has been contacted with a test agent. This net ratio in the first cell is then compared to the net ratio of a second cell which has not been contacted with the test agent (i.e., a control cell) to determine whether the agent modulates the subcellular localization of H11 kinase and therefore its activity. A predominant co-purification of H11 kinase with or localization of H11 kinase to the nucleus in the presence of the test agent as compared to the control cell, indicates that the agent is useful in increasing cell survival or growth. Conversely, a predominant co-purification of H11 kinase with or localization of H11 kinase to the cytosol in the presence of the test agent as compared to the control cell, indicates that the agent is useful in increasing cell death (i.e., decreases cell survival or growth). As used herein, predominant is intended to mean that more than 50% of the total cellular H11 kinase is present in the particular subcellular location.

An agent identified in accordance with the screening method of the present invention may further be assayed for its effect on cell growth or survival using any well-established method for measuring cell numbers or viability. For example, cell growth can be determined by counting cell numbers or by measuring the optical density before and after exposure of said cells to a test agent. Cell survival can be determined by, for example, measuring metabolic activity of the cell or cellular uptake of stains (e.g., propidium iodide staining of dying cells may increase in the presence of an agent which increases the ratio of H11 kinase localized in the cytosol).

Agents identified herein as modulators of cell growth or survival are useful in improving cardiac muscle strength or protecting the heart from damage. Diseases which may be prevented or treated using a agent of the invention include, but are not limited to, cardiovascular diseases or disorders, including atrial fibrillation, unstable angina, coronary artery disease, peripheral artery disease, cardiac allograft vasculopathy (CAVD); stroke; tissue infarction; lumbosciatic;

infection (bacterial, viral and protozoan); trauma; surgery; and Congestive Heart Failure (CHF).

Alternatively, modulators of cell growth or survival are useful in preventing or treating melanoma or other deleterious cell growth.

Thus, agents identified in accordance with the assay method of the invention can be combined with pharmaceutically acceptable carriers for use as therapeutic compositions. Examples of such carriers and methods of formulation of pharmaceutically acceptable compositions containing inhibitors and carriers can be found in Remington: The Science and Practice of Pharmacy, Alfonso R. Gennaro, editor, 20th ed. Lippincott Williams & Wilkins: Philadelphia, Pa., 2000. To form a pharmaceutically acceptable composition suitable for effective administration, such compositions will contain an effective amount of the agent.

Therapeutic or prophylactic compositions are administered to an individual in amounts sufficient to treat or prevent a disease of interest. The effective amount can vary according to a variety of factors such as the individual's condition, weight, sex and age. Other factors include the mode of administration. The appropriate amount can be determined by a skilled physician.

Compositions can be used alone at appropriate dosages. Alternatively, co-administration or sequential administration of other agents can be desirable.

The compositions can be administered in a wide variety of therapeutic dosage forms in conventional vehicles for administration. For example, the compositions can be administered in such oral dosage forms as tablets, capsules (each including timed release and sustained release formulations), pills, powders, granules, elixirs, tinctures, solutions, suspensions, syrups and emulsions, or by injection. Likewise, they can also be administered in intravenous (both bolus and infusion), intraperitoneal, subcutaneous, topical with or without occlusion, or intramuscular form, all using forms well-known to those of ordinary skill in the pharmaceutical arts.

Advantageously, compositions can be administered in a single daily dose, or the total daily dosage can be administered in divided doses of two, three or four times daily. Furthermore, compositions can be administered in intranasal form via topical use of suitable intranasal vehicles, or via transdermal routes, using those forms of transdermal skin patches well-known to those of ordinary skill in that art. To be administered in the form of a transdermal delivery system, the dosage administration will, of course, be continuous rather than intermittent throughout the dosage regimen.

The dosage regimen utilizing the compositions is selected in accordance with a variety of factors including type, species, age, weight, sex and medical condition of the patient; the severity of the condition to be treated; the route of administration; the renal, hepatic and cardiovascular function of the patient; and the particular composition thereof employed. A physician or veterinarian of ordinary skill can readily determine and prescribe the effective amount of the composition required to prevent, counter or arrest the progress of the condition. Optimal precision in achieving concentrations of composition within the range that yields efficacy without toxicity requires a regimen based on the kinetics of the composition's availability to target sites. This involves a consideration of the distribution, equilibrium, and elimination of a composition.

Having identified that a mutated, hyperactive from of H11 kinase is found in cancer cells, the present invention also provides a method for diagnosing a cancer associated with H11 kinase or Akt activation (e.g., prostate cancer, gastric cancer, melanoma, breast cancer, and the like). The diagnostic method of the present invention involves detecting the presence of a $Trp^{51} \rightarrow Cys$ mutant of H11 kinase of SEQ ID NO:1 in a sample from a patient. As used herein, detecting the presence of a $Trp^{51} \rightarrow Cys$ mutant of H11 kinase is intended to mean that the mutation can be detected at the nucleic acid or protein level.

A sample (i.e., blood, plasma, tissue, and the like) for use in the method of the invention can be isolated from a patient suspected of having or at risk of having a cancer associated with H11 kinase or Akt activation. Patients suspected of having a cancer associated with H11 kinase or Akt activation may exhibit one or more of the typical signs or symptoms associated with the disease including, e.g., tumor size, feelings of weakness, and pain perception. Patients at risk of having a cancer associated with H11 kinase or Akt activation include those with a family member or relative with such a cancer or individuals who have had cancer in the past and are in remission.

The $G \rightarrow C$ nucleic acid conversion resulting in the $Trp^{51} \rightarrow Cys$ mutant of H11 kinase can be detected using any well-established method including, but not limited to, amplified fragment length polymorphism (AFLP), restriction fragment analysis by CLEAVASE® Fragment Length Polymorphism (CFLP®), single-strand conformation polymorphism (SSCP), DNA sequencing, heteroduplex analysis (see, e.g., U.S. Pat. Nos. 6,024,878 and 6,287,822 and WO 92/086448), or hybridization to an array of oligonucleotide probes (see, e.g., U.S. Pat. No. 6,586,186).

Wherein the detection step employs one or more oligonucleotides, said oligonucleotide(s) can be selected from any region of the gene sequence encoding H11 kinase so long as the oligonucleotide(s) will either hybridize with nucleic acid sequences of the $G \rightarrow C$ nucleic acid conversion or flank the polymorphism thereby allowing for amplification of the polymorphism. Desirably, an oligonucleotide is selected for having an optimal annealing temperature, length and/or product yield. It is contemplated that a suitable oligonucleotide can be in the range of 10-600 bp.

When selecting a suitable oligonucleotide to PCR amplify a section of the H11 kinase gene, the specificity and annealing temperature and time are at least partly dependent on primer length. In general, oligonucleotides between 18 and 30 bases are desirable as this length of oligonucleotide is typically sequence-specific at optimal annealing temperature. A primer with an annealing temperature of at least 50° C. is preferable. In general, the annealing temperature is 5° C. lower than the melting temperature, the temperature at which 50% of the base pairs in a DNA fragment have separated. Thus, for an annealing temperature of at least 50° C., a primer with a calculated melting temperature ($T_m$) ~55-60° C. is desirable and may be tested empirically to confirm the optimal temperature. Further, it is desirable that oligonucleotide primers of a primer set have similar melting temperatures for efficient amplification of the desired product. The melting temperatures of oligonucleotide primers can be calculated using the nearest neighbor thermodynamic calculations. This is most easily accomplished using any of a number of primer design software packages (see, Sharrocks, A. D., In *PCR Technology, Current Innovations*, Griffin, H. G., and Griffin, A. M, Ed., CRC Press, London, 1994, pp. 5-11). Alternatively, a working approximation of this value (generally valid for oligonucleotides in the 18-30 base range) may be calculated using the formula: $T_m=2(A+T)+4(G+C)$.

In addition to optimal melting temperatures of the oligonucleotides, it is desirable to have the melting temperature of the product low enough to ensure 100% melting during the denaturation step of PCR (92-95° C.). In general, products between 100-600 base pairs are efficiently amplified in many PCR reactions.

It is desirable that the primers do not have self- or inter-primer homology as partially double-stranded structures and primer dimers may occur which will interfere with annealing to the template and product formation. Further, an oligonucleotide can be labeled, for example with a fluorophore.

When the step of detecting the G→C nucleic acid conversion includes PCR amplification, said PCR can be carried out using any standard PCR reaction reagents and conditions. Various factors such as temperature, magnesium ion concentration, DNA polymerase concentration and dNTP concentration must be considered for a suitable replication fidelity and reaction rate. Moreover, to reduce the likelihood of introducing artifactual mutations as a result of PCR amplification, a proofreading DNA polymerase such as Pho polymerase is preferred. Other suitable DNA polymerases include Taq, Tac, Tne, Pwo, Kod, Sac, Mth, Tth, ES4, VENT, DEEPVENT, PFUTurbo, AmpliTaq. A detailed discussion of PCR amplification is provided by Eckert, et al., in *PCR: A Practical Approach*, McPherson, Quirke, and Taylor, eds., IRL Press, Oxford, 1991, pp. 225-244.

Wherein the step of detecting a $Trp^{51}$→Cys mutant of H11 kinase involves detecting the mutant protein, an antibody which specifically recognizes the mutant is desirably used. Accordingly, the present invention further provides an antibody which specifically recognizes a $Trp^{51}$→Cys mutant of H11 kinase.

An antibody is said to specifically recognize a $Trp^{51}$→Cys mutant of H11 kinase if it is able to discriminate between wild-type (i.e., having a Trp at position 51) and mutant (i.e., having a Cys at position 51) forms of H11 kinase and bind mutant H11 kinase to form an H11 kinase-antibody complex, i.e., antigen-antibody complex.

Antibodies that specifically recognize a $Trp^{51}$→Cys mutant of H11 kinase can be of the monoclonal and polyclonal type. It is contemplated that such antibodies can be natural or partially or wholly synthetically produced. All fragments or derivatives thereof which maintain the ability to specifically recognize a $Trp^{51}$→Cys mutant of H11 kinase are also contemplated. The antibodies can be a member of any immunoglobulin class, including any of the classes: IgG, IgM, IgA, IgD, and IgE.

Antibody fragments can be any derivative of an antibody which is less than full-length. Desirably, the antibody fragment retains at least a significant portion of the full-length antibody's specific binding ability. Examples of antibody fragments include, but are not limited to, Fab, Fab', F(ab')$_2$, scFv, Fv, dsFv diabody, or Fd fragments. The antibody fragment can be produced by any means. For instance, the antibody fragment can be enzymatically or chemically produced by fragmentation of an intact antibody or it can be recombinantly produced from a gene encoding the partial antibody sequence. The antibody fragment can optionally be a single-chain antibody fragment. Alternatively, the fragment can comprise multiple chains which are linked together, for instance, by disulfide linkages. The fragment can also optionally be a multi-molecular complex. A functional antibody fragment will typically comprise at least about 50 amino acids and more typically will comprise at least about 200 amino acids. As used herein, an antibody also includes bispecific and chimeric antibodies.

Naturally produced antibodies can be generated using well-known methods (see, e.g., Kohler and Milstein (1975) *Nature* 256:495-497; Harlow and Lane, In: Antibodies: A Laboratory Manual, Cold Spring Harbor Laboratory, New York (1988)). Alternatively, H11 kinase antibodies which specifically recognize a $Trp^{51}$→Cys mutant of H11 kinase are derived by a phage display method. Methods of producing phage display antibodies are well-known in the art (e.g., Huse, et al. (1989) *Science* 246(4935):1275-81).

Selection of anti-$Trp^{51}$→Cys mutant of H11 kinase antibodies is based on binding affinity to a $Trp^{51}$→Cys mutant H11 kinase and can be determined by the various well-known immunoassays indicated above.

In general, a method of using antibodies which specifically recognize a $Trp^{51}$→Cys mutant of H11 kinase provides contacting a sample with said antibody and detecting the formation of an antigen-antibody complex using an immunoassay. The conditions and time required to form the antigen-antibody complex can vary and are dependent on the sample being tested and the method of detection being used. Once non-specific interactions are removed by, for example, washing the sample, the antigen-antibody complex is detected using any one of the well-known immunoassays used to detect and/or quantitate antigens. Exemplary immunoassays which may be used in the methods of the invention include, but are not limited to, enzyme-linked immunosorbent, immunodiffusion, chemiluminescent, immunofluorescent, immunohistochemical, radioimmunoassay, agglutination, complement fixation, immunoelectrophoresis, western blots, mass spectrometry, antibody array, and immunoprecipitation assays and the like which can be performed in vitro, in vivo or in situ. Such standard techniques are well-known to those of skill in the art (see, e.g., "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. (1984) *J. Clin. Chem. Clin. Biochem.* 22:895-904; Harlow and Lane, Antibodies: A Laboratory Manual, Cold Spring Harbor Laboratory, New York (1988) 555-612).

These immunoassays typically rely on labeled antigens, antibodies, or secondary reagents for detection. These proteins may be labeled with radioactive compounds, enzymes, biotin, or fluorochromes. Of these, radioactive labeling can be used for almost all types of assays. Enzyme-conjugated Labels are particularly useful when radioactivity must be avoided or when quick results are needed. Biotin-coupled reagents usually are detected with labeled streptavidin. Streptavidin binds tightly and quickly to biotin and can be labeled with radioisotopes or enzymes. Fluorochromes, although requiring expensive equipment for their use, provide a very sensitive method of detection. Those of ordinary skill in the art will know of other suitable labels which can be employed in accordance with the present invention. The binding of these labels to antibodies or fragments thereof can be accomplished using standard techniques (see, for example, Kennedy, et al. (1976) *Clin. Chim. Acta* 70:1-31 and Schurs, et al. (1977) *Clin. Chim Acta* 81:1-40).

The method of the invention can be employed as a component of a diagnostic or prognostic test to identify a cancer. It is contemplated that detection of a $Trp^{51}$→Cys mutant of H11 kinase can be applied as part of a general population screen, ideally at birth along with other neonatal screening or as part of a prenatal screen.

The invention is described in greater detail by the following non-limiting examples.

EXAMPLE 1

Mouse Model of Myocardial Ischemia

The generation of a cardiac-specific transgenic mouse overexpressing H11 kinase (FVB background) is well-known in the art (Depre et al. (2002) supra). Mice were anesthetized with pentobarbital sodium (60 mg/kg, ip) and ventilated. Ischemia was induced by ligating the anterior descending branch of the left coronary artery (LAD) using a 8-0 nylon suture, with a silicon tubing placed on top of the LAD, and confirmed by an ST elevation at the electrocardiogram. After occlusion for 20 to 60 minutes, the tubing was removed to achieve reperfusion for 4 to 24 hours. Ischemic preconditioning was triggered by six episodes of 4 minute occlusion followed by 4 minute reperfusion. Sham animals were treated similarly, without the suture around the LAD. Samples were immediately frozen in liquid nitrogen or fixed in 10% formalin. For the assessment of area-at-risk and infarct size, animals were re-anesthetized after 24 hours reperfusion. The heart was arrested at the diastolic phase by KCl injection, and the ascending aorta was perfused with saline to wash out blood. The LAD was occluded and 0.5% filtered Alcian blue dye was perfused through the coronary arteries (Ping et al. (2002) J. Clin. Invest. 109:499-507). Hearts were excised, rinsed in cold saline and sliced into 1-mm cross sections incubated with 1% triphenyltetrazolium Chloride at 37° C. for 15 minutes. Measurement of the infarct area and the area-at-risk from both sides of each section was performed with the IMAGE-PRO® software, and the values obtained from the different slices were averaged for each heart.

Wortmannin (Sigma, St. Louis, Mo.) was diluted in 10% DMSO/90% saline and injected i.p. at a dose of 3 mg/kg twice daily during three days.

EXAMPLE 2

Swine Model of Myocardial Ischemia

Myocardial ischemia was induced in adult swine by a hydraulic occluder implanted around the base of the LAD artery (Kim et al. (2003) Circ. Res. 92:1233-1239). Myocardial blood flow through the LAD was monitored by a transonic flow probe. After 3-5 days of recovery, ischemia was induced in the conscious animal by inflating the coronary occluder to reduce the blood flow in the LAD by 40% from baseline. The coronary stenosis was maintained for 90 minutes followed by complete deflation of the occluder and full reperfusion for 12 hours; that sequence was repeated five times. Myocardial samples were taken from both the ischemic area and the remote area of the beating heart, and were immediately used for protein extraction, as described herein.

EXAMPLE 3

Protein Extraction and Western Blot Analysis

Homogenization was performed using standard methods (Depre et al. (2002) supra). For cell fractionation, whole hearts were homogenized manually in a hypotonic buffer (10 mM Tris-HCl pH 7.5, 1 mM $MgCl_2$, protease inhibitors cocktail). The homogenate was spun at 100×g for 5 minutes and the initial pellet was discarded. Cell fractions were separated by sequential centrifugations at 4° C., including: 500×g for 5 minutes (nuclei), 20,000×g for 10 minutes in the presence of 0.25 M sucrose/15 mM NaCl (mitochondria), 100,000×g for 90 minutes (plasma membrane). Protein extracts were resolved by sodium dodecyl sulfate polyacrylamide gel electrophoresis (SDS-PAGE), transferred to nitrocellulose membranes and probed with the different primary antibodies. After washing and incubation with the secondary antibody, detection was performed with the enhanced chemiluminescence reagents (New England Biolabs, Beverly, Mass.).

Protein A-sepharose was incubated overnight at 4° C. with 1 μg of antibody, incubated at 4° C. with the cell extracts for 2 hours and washed in phosphate-buffered saline. Proteins were denatured, resolved on SDS-PAGE gels and transferred. Antibodies were added at the recommended dilution and detected by chemiluminescence.

EXAMPLE 4

Electrophysiology

In both wild-type and transgenic mice, myocytes were isolated using well-established methods (Kim et al. (1999) J. Clin. Invest. 103:1089-1097). Hearts were removed and canulated for perfusion with collagenase 1 and 2 (Worthington Biochemical Corp., Freehold, N.J.) in a Tyrode solution bubbled with 95% $O_2$/5% $CO_2$ for 15 minutes. Subsequently, the heart tissue was minced and further dissociated by shaking. Intact cardiac cells were enriched by centrifugation at 100 rpm for 1 minute. Whole cell currents were recorded using patch-clamp techniques (Masaki et al. (1997) Am. J. Physiol. 272:H606-H612). Cell capacitance was measured using voltage ramps of 0.8 V/s from a holding potential of −50 mV (Yatani et al. (1999) J. Mol. Cell. Cardiol. 31:1327-1336).

EXAMPLE 5

Histology

Samples from transgenic mice and wild-type littermates were fixed in 10% formalin. Silver staining of methacrylate-embedded transversal sections of the hearts was performed to detect myocyte outlines. Myocyte cross-sectional area was compared in transgenic and wild-type mice and quantified using the METAMORPH® Image Software System (Universal Imaging, Westchester, Pa.). Suitable cross sections were defined as having circular capillary profiles and circular to oval myocyte sections.

EXAMPLE 6

Cell Culture

Primary cultures of ventricular cardiac myocytes were prepared from 1-day-old Wistar rats (Charles River Laboratories, Wilmington, Mass.) (Depre et al. (2003) supra), and plated at a density of $10^6$ cells/$cm^2$. Cells were cultured in Modified Eagle Medium (DMEM)/F12. After 24 hours, myocytes were cultured in serum-free medium. A recombinant adenovirus expressing H11 kinase was constructed (Depre et al. (2002) supra). Titers were determined on 293 cells overlaid with Dulbecco's Modified Eagle Medium (DMEM) plus 5% equine serum and 0.5% agarose. Cells were infected with recombinant adenoviruses expressing H11 kinase (5 MOI) or the β-gal control were added to the cells for 36 hours before measurements were taken. Caspase-3 measurements were performed in accordance with standard methods (Depre et al. (2003) supra).

EXAMPLE 7

Purification of H11 Kinase

The H11 kinase coding sequence was subcloned in His-tagged pET-23a-d(+) vector (INVITROGEN™, Carlsbad, Calif.) and transfected into E. coli. The protein was purified from a PROBOND™ resin column. A second purification was performed by ion exchange chromatography and elution in a 0-1 M NaCl gradient.

EXAMPLE 8

Apoptosis

TUNEL staining was performed in formalin-fixed tissue (Depre, et al. (2004) supra). Positive nuclei from cardiac myocytes were counted in the area-at-risk. Small-size fragmented DNA was extracted (TACS™ apoptosis detection kit; R&D Systems, Minneapolis, Minn.), separated on 1.5% agarose gel and visualized with ethidium bromide.

EXAMPLE 9

Biochemical Assays

AMPK activity was measured using standard methods (Marsin, et al. (2000) Curr. Biol. 10:1247-1255). PKCε activity was measured using the PKC BIOTRAK® assay system (Amersham Pharmacia Biotech, Piscataway, N.J.). Fru-2,6-bis P was measured according to standard protocols (Depre, et al. (1993) supra).

EXAMPLE 10 cDNA Microarray Analysis

Synthesis of cDNAs (SUPERSCRIPT™; INVITROGEN™, Carlsbad, Calif.) was performed with 10 μg total RNA using a T7-oligo(24) dT primer. The DNA was transcribed into biotin-labeled RNA (BIOARRAY™ RNA Labeling Kit; ENZO Life Sciences, Farmingdale, N.Y.) and hybridized on mouse micro-array (430.2.0 GENECHIP®; AFFYMETRIX®, Santa Clara, Calif.). Data analysis was performed with the Microarray Analysis Suite (AFFYMETRIX®, Santa Clara, Calif.). The fold change was averaged from all the samples for which the signal was above background.

EXAMPLE 11

Statistical Analysis

Results are presented as the mean ±SEM for the number of samples indicated. Statistical comparison was performed using the Student's t test. A value of $P<0.05$ was considered as significant.

---

What is claimed is:

1. A method for identifying an agent for increasing cardiac cell survival comprising:
   a) contacting a first cardiac cell containing H11 kinase with a test agent;
   b) determining the net ratio of nuclear-localized versus cytosolic-localized H11 kinase in said first cell;
   c) determining the net ratio of nuclear-localized versus cytosolic-localized H11 kinase in a second cardiac cell that has not been contacted with said test agent; and
   d) comparing the difference between the net ratio of nuclear-localized versus cytosolic-localized H11 kinase in the first cell as compared with the second cell wherein an increase in said ratio in the first cell as compared to the ratio in the second cell indicates that the test agent increases cardiac cell survival.

2. A method for identifying an agent for increasing cardiac cell survival comprising:
   a) contacting a first cardiac cell containing H11 kinase encoded by the nucleic acid of SEQ ID NO:2 or 3 with a test agent;
   b) determining the net ratio of nuclear-localized versus cytosolic-localized H11 kinase in said first cell;
   c) determining the net ratio of nuclear-localized versus cytosolic-localized H11 kinase in a second cardiac cell that has not been contacted with said test agent; and
   comparing the difference between the net ratio of nuclear-localized versus cytosolic-localized H11 kinase in the first cell as compared with the second cell, wherein an increase in said ratio in the first cell as compared to the ratio in the second cell indicates that the test agent increases cardiac cell survival.

* * * * *

SEQUENCE LISTING

```
<160> NUMBER OF SEQ ID NOS: 7

<210> SEQ ID NO 1
<211> LENGTH: 196
<212> TYPE: PRT
<213> ORGANISM: Homo sapiens

<400> SEQUENCE: 1

Met Ala Asp Gly Gln Met Pro Phe Ser Cys His Tyr Pro Ser Arg Leu
1               5                   10                  15

Arg Arg Asp Pro Phe Arg Asp Ser Pro Leu Ser Ser Arg Leu Leu Asp
                20                  25                  30

Asp Gly Phe Gly Met Asp Pro Phe Pro Asp Asp Leu Thr Ala Ser Trp
            35                  40                  45

Pro Asp Trp Ala Leu Pro Arg Leu Ser Ser Ala Trp Pro Gly Thr Leu
    50                  55                  60

Arg Ser Gly Met Val Pro Arg Gly Pro Thr Ala Thr Ala Arg Phe Gly
65                  70                  75                  80

Val Pro Ala Glu Gly Arg Thr Pro Pro Pro Phe Pro Gly Glu Pro Trp
                85                  90                  95

Lys Val Cys Val Asn Val His Ser Phe Lys Pro Glu Glu Leu Met Val
                100                 105                 110

Lys Thr Lys Asp Gly Tyr Val Glu Val Ser Gly Lys His Glu Glu Lys
            115                 120                 125

Gln Gln Glu Gly Gly Ile Val Ser Lys Asn Phe Thr Lys Lys Ile Gln
        130                 135                 140

Leu Pro Ala Glu Val Asp Pro Val Thr Val Phe Ala Ser Leu Ser Pro
145                 150                 155                 160
```

```
Glu Gly Leu Leu Ile Ile Glu Ala Pro Gln Val Pro Pro Tyr Ser Thr
            165                 170                 175

Phe Gly Glu Ser Ser Phe Asn Asn Glu Leu Pro Gln Asp Ser Gln Glu
            180                 185                 190

Val Thr Cys Thr
        195

<210> SEQ ID NO 2
<211> LENGTH: 591
<212> TYPE: DNA
<213> ORGANISM: Homo sapiens

<400> SEQUENCE: 2
atggctgacg gtcagatgcc cttctcctgc cactacccaa gccgcctgcg ccgagacccc      60
ttccgggact ctcccctctc ctctcgcctg ctggatgatg gctttggcat ggaccccttc     120
ccagacgact tgacagcctc ttggcccgac tgggctctgc ctcgtctctc ctccgcctgg     180
ccaggcaccc taaggtcggg catggtgccc cggggcccca ctgccaccgc caggtttggg     240
gtgcctgccg agggcaggac cccccccacc ttccctgggg agccctggaa agtgtgtgtg     300
aatgtgcaca gcttcaagcc agaggagttg atggtgaaga ccaaagatgg atacgtggag     360
gtgtctggca acatgaaga gaaacagcaa gaaggtggca ttgttttctaa gaacttcaca     420 aagaaaatcc agcttcctgc agaggtggat cctgtgacag tatttgcctc actttcccca     480
gagggtctgc tgatcatcga agctcccag gtccctcctt actcaacatt tggagagagc     540
agtttcaaca cgagcttcc ccaggacagc caggaagtca cctgtaccta g               591

<210> SEQ ID NO 3
<211> LENGTH: 1811
<212> TYPE: DNA
<213> ORGANISM: Mus musculus

<400> SEQUENCE: 3
gagaagtttc taggctcgcg agtccccgag ctttattaaa ctcctggctg tgctcaagac      60
ctcagcaggc tttggctggg agccggggca gcctggaggg aaggcagccg gtggcttact     120
gatagccaag cgagagagag aggccctctg ggattctgct gggcccgctt agggaggggg     180
tcacctttgt aagccaggac cccagctcaa ttctgggcag ccagcggatg gttgggctcg     240
tggctgaagg aagatcagca ttttctgaag tggagaacta aattctgaaa gccatctcaa     300
gccacatcac cttgctgtgt gacctttggg taggtggctc tgtctctctg agcctctgtt     360
tccccctcta agttcgacca acatcatggc tgacgggcaa ttgccttttcc cgtgctccta     420 cccaagccgc ctgcgccgag accccttttcg ggactcaccg ctctcctccc gccttctgga     480
cgatggcttt ggcatggacc cttttccaga cgacttgaca gccccttggc cagagtgggc     540
tttgcctcgg ctctcctctg cctggcctgg aaccctaagg tctggcatgg taccccgagg     600
gcctccagcc acagctaggt ttggagtgcc cgctgagggc aggagtcccc caccccttccc     660 tggggagcct tggaaagtgt gtgtcaacgt gcacagcttc aagccggaag agctgatggt     720
aaagaccaag gatggatacg tggaagtttc aggcaaacat gaagagaagc agcaggaagg     780
tgggattgtc tccaagaact tcaccaagaa aatacagctc cctgcagaag tggatccagc     840
cactgtattt gcctcgcttt ctccagaggg cctgctcatc atcgaggctc cccaggtccc     900
tccgtactca ccctttggag agagcagctt caacaacgag cttcctcaag acaaccagga     960
agtcacctgt tcctaagacg tcagccttgg tccttcttcg ctcccatccc cagccccagg    1020
```

```
gactctctga tttgagggta cactacttta gcagcactca gatttaaggc aactcagatg    1080
ttgggggatg ggagggagaa ccgaacgacc gtccctggat gatgtagtaa tagatttctc    1140
cacagggtga cgcaatgggt cagccttgct tggttgcgtt aggtcaaagg attgggaggt    1200
ttttcttcat cttatctggg tgaagacgtc tcgcagtcta cagttgcaaa acaagcaaat    1260
ggggactgaa gatttcatgt taaattttta ccttgcagtt aatgcaagag ttgcttttct    1320
ctggggacct tcccatcacc cagatccctg ctctggaccc tccttctacg tggcttggtt    1380
gatgggactc attggctcac ctcagtgtgt ttctaaactc tttgtctaga agaggttatg    1440
ggcaggtctt atatccccat atgggattta tccttcacca cacaacacag tgccttttt     1500 tgcagcatga ccccatggct ctcaaaccat caccaccaag aactctggga gccctcagt     1560 taattctctg gctaaggtcc cccttttattg tgtccctgt gtccaagtca cattttaca    1620 gagagctgtc ttggagcagc tccgcaagga accaagcaaa ggccagacag cctgcacgca    1680
ggctagtggc attgtgtgtg tgtttgaggg gtggggagga tgtgtgtgtc tttgttgtgt    1740
gaattgtgct gttgtttaga gggaaaataa cggtgaataa taatgatgat aataaaggag    1800
ctgatgttcc t                                                         1811

<210> SEQ ID NO 4
<211> LENGTH: 51
<212> TYPE: DNA
<213> ORGANISM: Homo sapiens

<400> SEQUENCE: 4
gacttgacag cctcttggcc cgactgcgct ctgcctcgtc tctcctccgc c              51

<210> SEQ ID NO 5
<211> LENGTH: 17
<212> TYPE: PRT
<213> ORGANISM: Homo sapiens

<400> SEQUENCE: 5

Asp Leu Thr Ala Ser Trp Pro Asp Cys Ala Leu Pro Arg Leu Ser Ser
1               5                   10                  15

Ala

<210> SEQ ID NO 6
<211> LENGTH: 51
<212> TYPE: DNA
<213> ORGANISM: Homo sapiens

<400> SEQUENCE: 6
gacttgacag cctcttggcc cgactgggct ctgcctcgtc tctcctccgc c              51

<210> SEQ ID NO 7
<211> LENGTH: 17
<212> TYPE: PRT
<213> ORGANISM: Homo sapiens

<400> SEQUENCE: 7

Asp Leu Thr Ala Ser Trp Pro Asp Trp Ala Leu Pro Arg Leu Ser Ser
1               5                   10                  15

Ala
```